United States Patent [19]

Tsuji et al.

[11] Patent Number: 4,581,173

[45] Date of Patent: Apr. 8, 1986

[54] PRODUCTION OF HYDROXYMETHYLBUTENOIC ACIDS VIA OXIDATION

[75] Inventors: Teruji Tsuji; Kanji Tokuyama; Mamoru Tanaka; Hiroyuki Ishitobi, all of Osaka, Japan

[73] Assignee: Shionogi & Co., Ltd., Osaka, Japan

[21] Appl. No.: 482,974

[22] Filed: Apr. 7, 1983

[30] Foreign Application Priority Data

Apr. 23, 1982 [JP] Japan ................................ 57-69402

[51] Int. Cl.$^4$ ...................... C07D 498/04; C07B 3/00
[52] U.S. Cl. ................................................. 260/245.4
[58] Field of Search ...................................... 260/245.4

[56] References Cited

PUBLICATIONS

Ashurov et al., Chem. Abs. 89, 42303u (1977).
Kyazimov et al., Chem. Abs. 78, 42814j (1972).
MacDonald et al., J. Amer. Chem. Soc. 102, 7760 (1980).
Frimer, J. Org. Chem. 42, p. 3194 (1977).
Hawley, "Condensed Chemical Dictionary" 8th edition p. 787.
Noss et al., Chem. Ber. 89, 2641, 2644 (1956).
Tobolsky et al., "Organic Peroxides" p. 13 (1954).

*Primary Examiner*—Mark L. Berch
*Attorney, Agent, or Firm*—Wenderoth, Lind & Ponack

[57] ABSTRACT

A useful industrial chemical, oxazolinoazetidinylhydroxymethylbutenoic acid derivative (II) can be produced by oxidizing the corresponding oxazolinoazetidinylhalomethylbutenoic acid derivative(I).

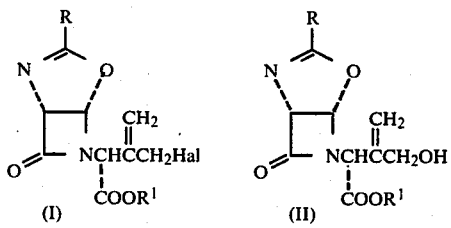

wherein R is an alkyl, aralkyl or aryl group,

R$^1$ is a hydrogen atom or a carboxy protecting group and Hal is a halogen atom.

9 Claims, No Drawings

PRODUCTION OF HYDROXYMETHYLBUTENOIC ACIDS VIA OXIDATION

INTRODUCTION

This invention relates to a substitution of halogen with hydroxy by the action of an oxidizing reagent. More specifically, it relates to oxidation of an oxazolinoazetidinylhalomethylbutenoic acid derivative (I) to give the corresponding oxazolinoazetidinylhydroxymethylbutenoic acid derivative (II) according to the following scheme

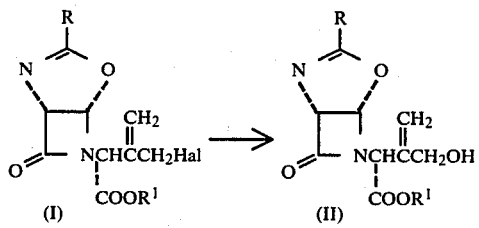

wherein R is an alkyl, aralkyl or aryl group,
$R^1$ is a hydrogen atom or a carboxy protecting group, and Hal is a halogen atom.

BACKGROUND OF THIS INVENTION

Known methods for converting a halomethyl compound to a hydroxymethyl compound generally use a hydrolysis of the corresponding iodomethyl compound.

Now, the present inventors have found that this conversion proceeds with oxygenation more economically and with a higher yield and as a result of this discovery they were led to this invention. They confirmed further that this reaction goes satisfactorily with an oxidizing agent even with diluted molecular oxygen, e.g., air.

USE OF THE PRODUCT (II)

The objective products (II) of this method are known to be useful as intermediates for synthesizing useful materials, e.g., oxacephem antibacterials (e.g., M. Yoshioka et al., Tetrahedron Letters, Vol. 21, pp. 351–354 (1980)).

DEFINITION OF THE SYMBOLS

The alkyl, aralkyl or aryl group R has preferably 1 to 12 carbon atoms and can be substituted by a group devoid of an adverse effect under the reaction condition of this invention, e.g., $C_1$ to $C_3$-alkyl, nitro, $C_1$ to $C_3$-alkoxy, monocyclic aryloxy, halogen or the like.

The halogen Hal can be chlorine, bromine or preferably, iodine.

The carboxy protecting group $R^1$ can be an ester forming group for protecting the carboxy group under the reaction conditions of this invention. Preferable groups $R^1$ are easily removable without adverse effect on the product (II) after the reaction of this invention, when desired.

Representatives of the $R^1$ group contain 1 to 20 carbon atoms and are well known in the chemistry of β-lactam antibacterials and include a group forming an alkyl ester, e.g., t-butyl, cyclopropylmethyl, allyl or 2,2,2-trichloroethyl ester; aralkyl ester, e.g., benzyl, methylbenzyl, dimethylbenzyl, methoxybenzyl, ethoxybenzyl, nitrobenzyl, aminobenzyl, diphenylmethyl, phthalidyl or phenacyl ester; aryl ester, e.g., phenyl, pentachlorophenyl or indanyl ester; ester with an N-hydroxyamino compound, e.g., an ester with acetone oxime, acetophenone oxime, acetaldoxime, N-hydroxysuccinimide or N-hydroxyphthalimide; or equivalently, it can be replaced by a group forming an acid anhydride with carbonic or carboxylic acid or an amide group.

These $R^1$ groups can further be substituted by a group devoid of an adverse effect on the reaction of this invention and can be ones as exemplified above in relation to the R group.

STARTING MATERIALS

The starting compounds (I) as defined above are known or analogous to those described in the cited Yoshioka et al. reference and other literature related to the field of β-lactam chemistry.

REACTIONS OF THIS INVENTION

As stated above, this invention is a substitution of halogen with hydroxy by the action of an oxidizing reagent. The reaction courses are illustrated below by reaction scheme

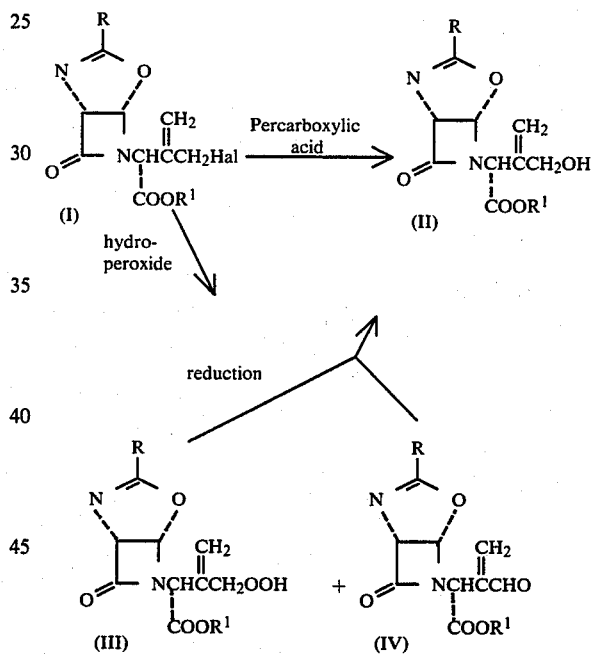

wherein R, $R^1$ and Hal are as defined above.

The oxidizing reagent can be a percarboxylic acid or its salt. This was at first believed to be a peroxide substitution as stated below under the item 8, but it is now believed to proceed through another pathway of the oxidation mechanism directly from the compounds (I) to (II).

Alternatively, it can be that capable of forming a hydroperoxide anion or radical with the aid of heat or literature. The produced oxazolinoazetidinylhydroperoxymethylbutenoic acid derivative (III) or oxazolinoazetidinylformylbutenoic acid derivative (IV) is reduced to give the hydroxymethyl compound (II).

PERCARBOXYLIC ACID OXIDATION

By way of the first course of percarboxylic acid oxidation, the compound (I), wherein Hal is iodine, is oxidized with a percarboxylic acid or its salt, e.g., peracetic acid, perpropionic acid, perbutyric acid, monoperphthalic acid, perbenzoic acid, m-chloroperbenzoic acid or salt thereof.

It is to be noted that in this oxidation, the halogen Hal is iodine.

Although it has not yet been scientifically proven, it is now believed that this course of reaction goes through oxidation of the iodine to iodoso group, then it rearranges to hypoiodide and succeeding oxidation to iodate and automatic hydrolysis gives the alcohol (II) and iodic acid. This course of the reaction is considered to be novel.

The reaction can be carried out in an inert industrial solvent, e.g., a water, hydrocarbon, halohydrocarbon, ketone, ester, amide or alcohol solvent or a mixture of these. For example, the solvent can be benzene, dichloromethane, chloroform, carbon tetrachloride, acetone, methyl ethyl ketone, methyl isobutyl ketone, cyclopentanone, cyclohexanone, ethyl acetate, ethyl carbonate, ethylene carbonate, N,N-dimethylformamide, hexamethylphosphorotriamide, 1-ethylpyrrolidin-2-one, 1,3-dimethylimidazolidin-2-one, acetonitrile, benzonitrile, dimethyl sulfoxide, isopropanol, ethanol, methanol, water or a mixture of these.

Among these, more preferable are water, halohydrocarbon and ester solvents, e.g., water, ethyl acetate, dichloromethane, chloroform or carbon tetrachloride.

The reaction can be accelerated by a base, preferably an inorganic base, e.g., alkali metal carbonate or hydrogencarbonate to catch the iodine acid formed during the reaction. Further, the reaction can preferably be done in a medium consisting of two phases, e.g., aqueous and water-immiscible solvent layers. The latter phase serves for dissolving the inorganic salt formed in the reaction. Slightly soluble salts separate as a solid when the amount of the aqueous layer is small enough. The aqueous layer may also serve for dissolving the base to be added. Sodium iodate produced during the reaction can be removed by mere filtration.

The starting material (I) wherein Hal is iodine can be prepared from the corresponding compound (I) wherein Hal is chlorine or bromine by treating with an alkali metal iodide in a manner conventional in the art, i.e., by dissolving the starting material and an alkali metal iodide in a polar solvent. In this case, the compound (I) produced in the reaction mixture wherein Hal is iodine can be used directly for the percarboxylic acid oxidation as stated above without isolation.

The reaction mixture can be worked up in a conventional manner to yield the product (II) in high yield. Such a method for isolation and purification includes extraction, washing, drying, filtration, concentration, chromatography, adsorption, elution, partition and recrystallization.

PEROXIDE OXIDATION AND REDUCTION

(i) Oxidation

The oxidizing reagent for the hydroperoxide oxidation can be oxygen, diluted oxygen as air, hydrogen peroxide, metal peroxide or the like.

This reaction can be accelerated by the irradiation with e.g., a tungsten lamp, halogen lamp, mercury lamp or sunlight. This photoreaction can be assisted by a compound capable of being excited to a stable triplet state, i.e. photosensitizer, for example, iodine, a polynuclear aromatic hydrocarbon, e.g., benzanthracene, benzpyrene, chrysene or pyrene; a ketone, e.g., cyclopentanone, cyclohexanone or fluorenone; a pigment, e.g., eosin, fluorescein, methyl red or methyl yellow; other compound, e.g., phenothiazine; or other radical inducing method.

Alternatively, the reaction can be accelerated by heating at a temperature between 30° C. to 70° C., especially between 50° C. and 60° C. even in the dark, preferably in the presence of acetone, methyl ethyl ketone, acetonitrile, N-methylpyrrolidone, hexamethylphosphorotriamide, dimethylformamide, ethylene carbonate, diethyl carbonate or other radical-inducing method as exemplified for the irradiated hydroperoxide oxidation.

Both of the light and dark oxidations with a peroxide are carried out usually at a temperature between 0° C. and 100° C. for a duration between 10 minutes and 20 hours in a neutral or weakly basic medium for trapping the formed hydrogen halide and with stirring or bubbling.

The reaction is carried out in an inert industrial solvent as exemplified for the percarboxylic acid oxidation.

When oxygen is the oxidizing reagent, the main product is an aldehyde (IV). When hydrogen peroxide is the oxidizing reagent, the main product is a hydroperoxide (III) and when oxygen is the oxidizing reagent in the presence of an acid and sodium iodide, a hydroperoxide (III) is the main product, but it is then reduced by the reaction of 8 (ii) to give an alcohol (II).

The product (III) or (IV) can be isolated and purified by a conventional method, e.g., extraction, washing, drying, chromatography, crystallization or the like, or alternatively can be subjected to the reduction (ii) of the next step simultaneously in the reaction mixture or successively without isolation.

(ii) Reduction

The product (III) or (IV) can be reduced to give the objective hydroxy compound (II).

The reduction is carried out by the action of a reducing reagent capable of producing a hydroxymethyl compound (II) from a hydroperoxymethyl compound (III) or an aldehyde compound (IV) in a manner conventional in the art.

Representative reducing reagents for this purpose are those for reducing the hydroperoxide (III), for example, a trivalent phosphorus compound, e.g., phosphorous acid ester, trialkylphosphine or triarylphosphine (a tri-$C_1$ to $C_4$-alkyl phosphite, tri-$C_1$ to $C_4$-alkylphosphine, tri-monocyclic aryl-phosphine or the like) or an iodide salt plus an acid, e.g., sodium, potassium, calcium or ammonium iodide plus an acid, preferably a carboxylic acid (acetic acid, dehydroacetic acid, propionic acid, oxalic acid, benzoic acid or the like); and for reducing an aldehyde (IV), e.g., an alkali metal borohydride, alkali metal aluminum hydride, alkali metal (mono- or di-)alkoxyaluminum hydride, borane, alkylborane, aminoborane or the like.

The reduction can be carried out usually at a temperature between −50° C. and 100° C. for a duration between 10 minutes and 5 hours in an inert solvent selected from these as described for the oxidation (i) as above, if required with stirring or under inert gas, e.g., nitrogen or vapour of the solvent used.

EXAMPLES

Following examples are given to show the embodiments of this invention. In the Tables, the following abbreviations are used.

| | |
|---|---|
| Ac = acetyl, | BH = diphenylmethyl, |
| DHA = dehydroacetic acid, | equiv = equivalent |
| Et = ethyl, | m-CPBA = m-chloroperbenzoic acid, |
| min = minute, | Ph = phenyl, |
| rt = room temperature, | temp = temperature, |
| THF = tetrahydrofuran, | and wt = weight. |

EXAMPLE 1

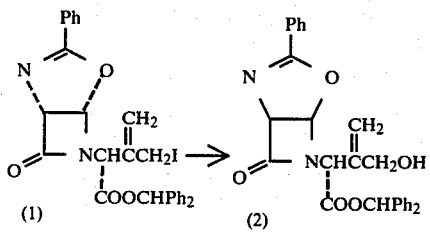

To a mixture of (2R)-2-[(1R,5S)-3-phenyl-7-oxo-4-oxa-2,6-diazabicyclo[3.2.0]hept-2-en-6-yl]-3-iodomethyl-3-butenoic acid diphenylmethyl ester (1) in an organic solvent and inorganic base in water is added a peracid portionwise under nitrogen gas, and the mixture is stirred for the given time at the given temperature under nitrogen. The reaction mixture is washed with water, aqueous 5% sodium thiosulfate, aqueous sodium hydrogen carbonate and water, dried over sodium sulfate and concentrated under reduced pressure. The residue is crystallized from ethanol to give (2R)-2-[(1R,5S)-3-phenyl-7-oxo-4-oxa-2,6-diazabicyclo[3.2.0]-hept-2-en-6-yl]-3-hydroxymethyl-3-butenoic acid diphenylmethyl ester (2). mp. 100°–104° C.

The reaction conditions are summarized on Table I.

EXAMPLE 2

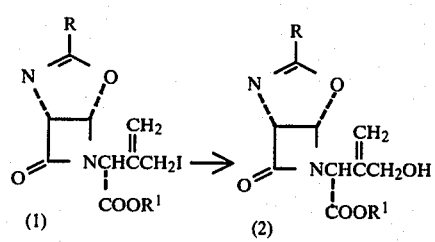

In a manner similar to that of Example 1, (2R)-2-[(1R,5S)-3-R-7-oxo-4-oxa-2,6-diazabicyclo[3.2.0]hept-2-en-6-yl]-3-iodomethyl-3-butenoic acid $R^1$ ester (1) is oxidized to afford (2R)-2-[(1R,5S)-3-R-7-oxo-4-oxa-2,6-diazabicyclo[3.2.0]hept-2-en-6-yl]-3-hydroxymethyl-3-butenoic acid $R^1$ ester (2).

R=p-tolyl, $R^1$=diphenylmethyl mp. 124°–126° C.
R=benzyl, $R^1$=t-butyl mp. 85°–87° C.

EXAMPLE 3

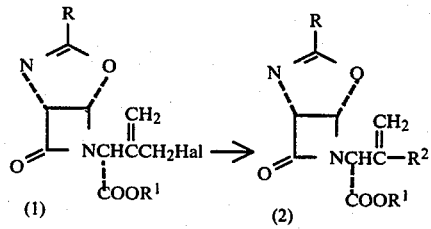

A solution of (2R)-2-[(1R,5S)-3-R-7-oxo-4-oxa-2,6-diazabicyclo[3.2.0]hept-2-en-6-yl]-3-halomethyl-3-butenoic acid $R^1$ ester (1) and an additional reagent in a solvent is stirred in the presence of a solution of the oxidizing reagent or a bubbling gaseous oxidizing reagent, if specified under the irradiation with a high voltage mercury lamp or halogen lamp. The organic layer is washed with aqueous sodium thiosulfate, aqueous sodium hydrogen carbonate and water, dried and concentrated to give the corresponding (2R)-2[(1R,5S)-3-R-7-oxo-4-oxa-2,6-diazabicyclo[3.2.0]-hept-2-en-6-yl]-3-$R^2$-3-butenoic acid $R^1$ ester (2). Each of the components, if any, can be separated by silica gel chromatography.

The reaction conditions are given on Table II and the physical constants of the products are given on Table III.

In the presence of sodium iodide and acid, the products are reduced simultaneously by a reduction of Table III, and the main product isolated is the compound (2) where $R^2$ is hydroxymethyl.

TABLE I
REACTION CONDITIONS OF THE PEROXIDE OXIDATION

| peracid (equiv.) | base (equiv.) | | solvent (ratio/weight) | temp (°C.) | time (hr) | yield (%) |
|---|---|---|---|---|---|---|
| | NaHCO₃ | (2.0) | EtOAc—H₂O(2:1/9) | rt | 2 | 88 |
| | NaHCO₃ | (2.0) | CH₂Cl₂—H₂O(2:1/30) | 5–10 | 1 | 82 |
| | — | (2.0) | EtOAc—H₂O(2:1/15) | rt | 2 | 71 |
| | — | (2.5) | Dioxan—H₂O(10:1/5) | 40 | 1 | — |
| PhCO₃H(4.5) | NaHCO₃ | (2.0) | EtOAc—H₂O(2:1/20) | rt | 3 | 88 |
| o-HOOCC₆H₄CO₃H(5.0) | NaHCO₃ | (2.0) | EtOAc—H₂O(100:1/20) | rt | 2.5 | 84 |
| CH₃CO₃H(6.0) | NaHCO₃ | (2.0) | EtOAc—H₂O(1:1/16) | rt | 17 | 93 |
| CH₃CO₃H(6.0) | NaHCO₃ | (2.0) | CH₂Cl₂—H₂O(1:1/16) | rt | 7 | 93 |
| CH₃CO₃H(6.0) | NaHCO₃ | (3.0) | CH₂Cl₂—H₂O(1:1/16) | rt | 7 | 70 |
| CH₃CO₃H(3.0) | K₂CO₃ | (2.0) | PhH—H₂O(2:1/5) | rt | 20 | — |
| CH₃CO₃H(10.0) | KHCO₃ | (5.0) | THF—H₂O(1:1/5) | 0 | 2 | — |

TABLE II

OXYGEN INTRODUCTION
with hydroperoxy radical

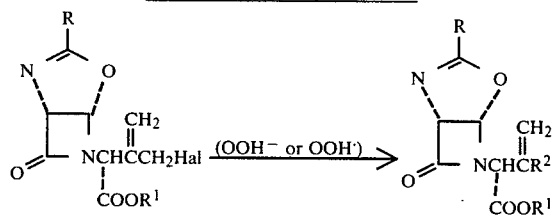

| Ex. No. | R | Hal | R[1] | Solvent (part by wt) | | oxidizing reagent (equiv) | hv | additional reagent (equiv) | Time (min) | Temp (°C.) | Yield (%) for R[2] | | |
|---|---|---|---|---|---|---|---|---|---|---|---|---|---|
| | | | | | | | | | | | CH$_2$OOH | CHO | CH$_2$OH |
| 1 | Ph | I | BH | EtOAc (50 × 2) | H$_2$O (5 × 2) | air | hv | NaHCO$_3$ (1 × 2) | 120 | 20 | — | 80 | — |
| 2 | Ph | I | BH | EtOAc (50 × 2) | H$_2$O (10 × 2) | 30% H$_2$O$_2$ (10 × 2) | hv | NaHCO$_3$ (1.3 × 2) | 60 | 20 | 78 | 125 | 8 |
| 3 | C$_6$H$_4$CH$_3$ | I | BH | EtOAC (90) | H$_2$O (7) | O$_2$ | hv | DHA + NaI* (5)   (5) | 480 | 0 | 26 | 52 | 3 |
| 4 | CH$_2$Ph | Cl | t-C$_4$H$_9$ | EtOAc (18) | — | O$_2$ | hv | DHA + NaI (3.5)  (3.7) | 480 | 50 | — | — | 74** |
| 5 | Ph | Br | BH | EtOAc (9) | 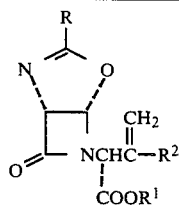 (9) | air | — | DHA + NaI (5.7)  (7.3) | 960 | 50 | — | — | 71** |
| 6 | Ph | I | BH | EtOAc (60) | — | O$_2$ | hv | HOAc + NaI (5.6)  (3.3) | 180 | rt | — | — | 76** |
| 7 | Ph | Cl | BH | EtOAc (9) | H$_2$O (5) | m-CPBA (4.7) | hv | NaI (2.0) | 120 | rt | — | — | 71** |
| 8 | Ph | I | BH | CH$_2$Cl$_2$ (30) | H$_2$O (10) | O$_2$ | hv | HOAc + NaI (5.3)  (9) | 400 | rt | — | — | 77** |

*In the presence of 0.26 molar equivalents of fluorescein
**After reduction of Table IV.

TABLE III

PHYSICAL CONSTANTS OF THE INTERMEDIATES

| No. | R | R[1] | R[2] | m.p. (°C.) | IR(CHCl$_3$) $\nu$: cm$^{-1}$ | NMR (CDCl$_3$) δ: ppm |
|---|---|---|---|---|---|---|
| 1 | Ph | | CHO | | 2820, 1780, 1750, 1695. | 5.35(s, 1H), 5.27(d,J = 3.5Hz, 1H), 5.90(d,J = 3.5Hz, 1H), 6.30(s, 1H), 6.52(s, 1H), 6.87(s, 1H), 7.0–8.1(m, 15H), 9.58(s, 1H). |
| 2 | Ph | | CH$_2$OOH | | 1770, 1750, 1630. | 4.52(s, 2H), 5.12(s, 1H), 5.32 (d,J = 3Hz, 1H), 5.43(s, 1H), 5.55(s, 1H), 6.20(d,J = 3Hz, 1H), 6.93(s, 1H), 7.18–8.00(m, 15H). |
| 3 | C$_6$H$_4$CH$_3$ | | CHO | 135–136° | 2825, 1786, 1755, 1700. | 2.34(s, 3H), 5.27(d,J = 3.5Hz, 1H), 5.34(s, 1H), 5.89(d,J = 3.5Hz, 1H), 6.36(s, 1H), 6.53(s, 1H), 6.87 (s, 1H), 7.1–7.9(m, 14H), 9.59 (s, 1H). |
| 4 | C$_6$H$_4$CH$_3$ | BH | CH$_2$OOH | | 1780, 1752, 1630. | 2.38(s, 3H), 4.50(s, 2H), 5.10 (s, 1H), 2.58(d,J = 3Hz, 1H), 5.42 (s, 1H), 5.53(s, 1H), 6.20(d,J = 3Hz, 1H), 6.90(s, 1H), 7.1–7.9 (m, 14H). |

EXAMPLE 4

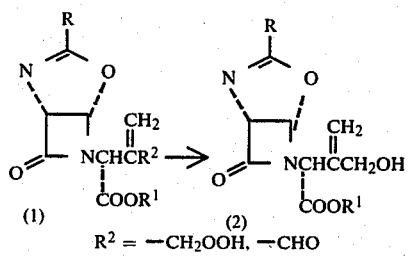

$R^2 = -CH_2OOH, -CHO$

To a solution of (2R)-2-[(1R,5S)-3-R-7-oxo-4-oxa-2,6-diazabicyclo[3.2.0]hept-2-en-6-yl]-3-$R^2$-3-butenoic acid $R^1$ ester (1) in a solvent is added a reducing reagent, and the mixture is stirred at the given temperature for the given time. The reaction mixture is washed with aqueous sodium hydrogen carbonate and water, dried and concentrated to remove the solvent. The residue is crystallized to give (2R)-2-[(1R,5S)-3-R-7-oxo-4-oxa-2,6-diazabicyclo[3.2.0]hept-2-en-6-yl]-3-$R^2$-3-butenoic acid $R^1$ ester.

The reaction condition is given on Table IV, and the physical constants are given on Examples 1 and 2.

TABLE IV
REDUCTION OF INTERMEDIATES

| Ex. No. | R | $R^1$ | Solvent (part by wt) | Reducing reagent (equiv.) | Temp. (°C.) | Time (min) | Yield* | $R^2$ |
|---|---|---|---|---|---|---|---|---|
| 1 | Ph | BH | THF + HOAc (12) (4) | NaBH$_4$ (5) | −50 | 60 | 83 C(1) | CHO |
| 2 | Ph | BH | EtOAc + H$_2$O (45) (5) | NaBH$_4$ (3.2) | 0 | 60 | 59 C(2) { | CHO / CH$_2$OOH |
|   |   |   |   | P(OCH$_3$)$_3$ (1.5) | 0 | 120 |   |   |
| 3 | CH$_3$C$_6$H$_4$ | BH | EtOAc + H$_2$O (90) | NaI + DHA (3) (4) | rt | 30 | 82 C(3) { | CHO / CH$_2$OOH |
| 4 | Ph | BH | EtOAc (18) | PPh$_3$ (1.2) | rt | 30 | 72 | CH$_2$OOH |
| 5 | CH$_3$C$_6$H$_4$ | BH | EtOAc (54) | NaI + HOAc (2.2) (4.9) | rt | 30 | 82 | CH$_2$OOH |
| 6 | PhCH$_2$ | t-C$_4$H$_9$ | EtOAc (18) | NaI + DHA (3.7) (3.5) | rt | 30 | 74 C(4) | CH$_2$OOH |
| 7 | Ph | BH | EtOAc + (9) (9) | NaI + DHA (7.3) (5.7) | rt | 20 | 71 C(5) | CH$_2$OOH |
| 8 | Ph | BH | EtOAc (60) | NaI + DHA (9.3) (5.6) | rt | 30 | 76 C(6) | CH$_2$OOH |
| 9 | CH$_3$C$_6$H$_4$ | BH | EtOAc (54) | NaI + HOAc (2.7) (4.7) | rt | 30 | 90 | CH$_2$OOH |
| 10 | Ph | BH | CH$_2$Cl$_2$ + H$_2$O (30) (10) | NaI + HOAc (9) (5.3) | rt | 20 | 77 C(8) | CH$_2$OOH |

*Yields with the mark C represent the yields are calculated on the reactions of Tables II and IV done continuously in which intermediate products were not isolated. Numbers in parentheses show the example numbers in Table II.

What we claim is:

1. A process for preparing a compound of the formula

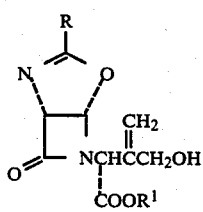

wherein R is alkyl, aralkyl or aryl, and
$R^1$ is a hydrogen atom or a protecting group which protects the carboxy group from degradation under the reaction conditions which comprises oxidizing, with an oxidizing reagent consisting of oxygen or hydrogen peroxide, a compound of the formula

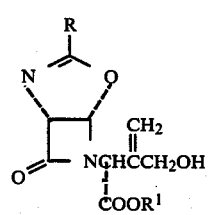

wherein R and $R^1$ are as defined above and Hal is a halogen atom, and subjecting the resultant product to reduction with a reducing agent selected from (a) triphenylphosphine or an iodide salt together with acid and (b) an alkali metal borohydride, an alkali metal aluminum hydride, a metal (mono- or di-)alkoxyaluminum hydride, borane, aminoborane or hydrocarbylborane.

2. A process for preparing a comound of the formula

[structure]

wherein R is an alkyl, aralkyl or aryl group, and
$R^1$ is a hydrogen atom or a protecting group which protects the carboxy group from degradation under the reaction conditions which comprises reacting a compound of the formula

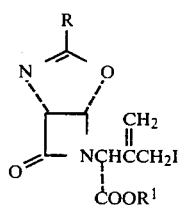

with a percarboxylic acid selected from (1) peracetic acid, (2) perpropionic acid, (3) perbutyric acid, (4) monoperphthalic acid, (5) perbenzoic acid, (6) m-chloroperbenzoic acid and (7) a salt of (1) to (6), said reaction being further carried out in the presence of an alkali metal carbonate and in a medium consisting of aqueous and water immiscible solvent phases.

3. A process as claimed in claim 2 wherein R is an alkyl, aralkyl or aryl group containing 1 to 12 carbon atoms which is unsubstituted or substituted by a group selected from $C_1$ to $C_3$-alkyl, nitro, $C_1$ to $C_3$-alkoxy, monocyclic aryloxy and halogen.

4. A process as claimed in claim 2 wherein $R^1$ is an alkyl, aralkyl or aryl ester forming group containing 1 to 20 carbon atoms.

5. A process as claimed in claim 2 wherein the oxidizing is carried out in a water and a halohydrocarbon or ester solvent.

6. A process as claimed in claim 1 wherein R is alkyl, aralkyl or aryl containing from 1 to 12 carbon atoms which is unsubstituted or substituted by $C_1$ to $C_3$-alkyl, nitro, $C_1$ to $C_3$-alkoxy, monocyclic aryloxy or halogen.

7. A process as claimed in claim 1 wherein Hal is chlorine or bromine.

8. A process as claimed in claim 1 wherein $R^1$ is an alkyl, aralkyl or aryl ester-forming group containing from 1 to 20 carbon atoms.

9. A process claimed in claim 1 wherein the reduction is carried out at a temperature between $-50°$ C. and $100°$ C. for 10 minutes to 5 hours in an inert gas.

* * * * *